US00PP33229P2

(12) United States Plant Patent
Ranney et al.

(10) Patent No.: US PP33,229 P2
(45) Date of Patent: Jul. 6, 2021

(54) ***VIBURNUM*PLANT NAMED 'NCVX4'**

(50) Latin Name: ***Viburnum davidii* x *propinquum***
Varietal Denomination: NCVX4

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/903,236

(22) Filed: Jun. 16, 2020

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226, 263.1
CPC ..... A01H 5/00; A01H 5/02; A01H 5/12
See application file for complete search history.

*Primary Examiner* — Kent L Bell
(74) *Attorney, Agent, or Firm* — Cassandra Bright

(57) ABSTRACT

A new and distinct cultivar of *Viburnum* plant named 'NCVX4' is disclosed, characterized by a compact habit and fragrant pink flowers. The new variety is a *Viburnum*, normally produced as an outdoor garden or container plant.

3 Drawing Sheets

Latin name of the genus and species: *Viburnum davidii* x *propinquum.*
Variety denomination: 'NCVX4'.

BACKGROUND OF THE INVENTION

The new *Viburnum* cultivar is a product of a planned breeding program conducted by the inventor in Mills River, N.C. The open-pollination resulting in this new variety was made during Summer of 2012. The objective of the breeding program was to develop new plant forms of *Viburnum* for commercial horticultural purposes.

The seed parent of 'NCVX4' is the unpatented, proprietary seedling referred to as *Viburnum* 'H2010-003-002'. The pollen parent is unidentified. The new variety was identified as a potentially interesting selection in the Summer of 2013, at a research greenhouse in Mills River, N.C.

The first asexual propagation of 'NCVX4' was carried out in July of 2014 by rooting stem cuttings at the same research greenhouse in Mills River, N.C. and has been asexually reproduced repeatedly. 'NCVX4' has been found to retain its distinctive characteristics through successive asexual propagations.

SUMMARY OF THE INVENTION

The cultivar 'NCVX4' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCVX4'. These characteristics in combination distinguish 'NCVX4' as a new and distinct *Viburnum* cultivar:

1. A compact habit with dense branching.
2. Fragrant pink flowers.
3. Semi-evergreen foliage.

PARENT COMPARISON

Plants of the new cultivar 'NCVX4' cannot be compared to the seed parent as records of the seed parent characteristics are not available.

The pollen parent is unidentified.

COMMERCIAL COMPARISON

Plants of the new cultivar 'NCVX4' can be compared to the commercial variety *Viburnum* 'Dawn', unpatented. These varieties are similar in most horticultural characteristics; however, 'NCVX4' differs in the following:

1. Plants of the new variety are smaller and more compact (150 to 200 cm tall and wide) than plants of 'Dawn' (about 300 cm tall).
2. Plants of 'NCVX4' are semi-evergreen, plants of this comparator are deciduous.

'NCVX4' can also be compared to 'NCVX2', U.S. Plant patent application Ser. No. 16/903,184. 'NCVX4' is smaller in size (height: 50 to 70 cm; width: 90 to 120 cm), with a more prostrate habit, smaller leaves (length 2.2 to 6 cm; width: 1 to 2.5 cm), and a larger inflorescence diameter (5 to 10 cm.). Compared to 'NCVX4', 'NCVX2' is larger in size (height: 80 to 120 cm; width: 100 to 120 cm), with a globose habit, larger leaves (length 4 to 9 cm; width: 1.5 to 3.7 cm), and a smaller inflorescence diameter (4 to 5 cm).

BRIEF DESCRIPTION OF THE PHOTOGRAPHS

This new smooth-leaf *Viburnum* (*Viburnum davidii* x *propinquum*) is illustrated by the accompanying photographs which show the plant's form, foliage and inflorescences. Plants illustrated are approximately 4 years old. The colors shown are as true as can be reasonably obtained by conventional photographic procedures. Colors in the photographs may differ slightly from the color values cited in the detailed botanical description, which accurately describe the colors of the new *Viburnum* cultivar.

DETAILED BOTANICAL DESCRIPTION

Figure 1:
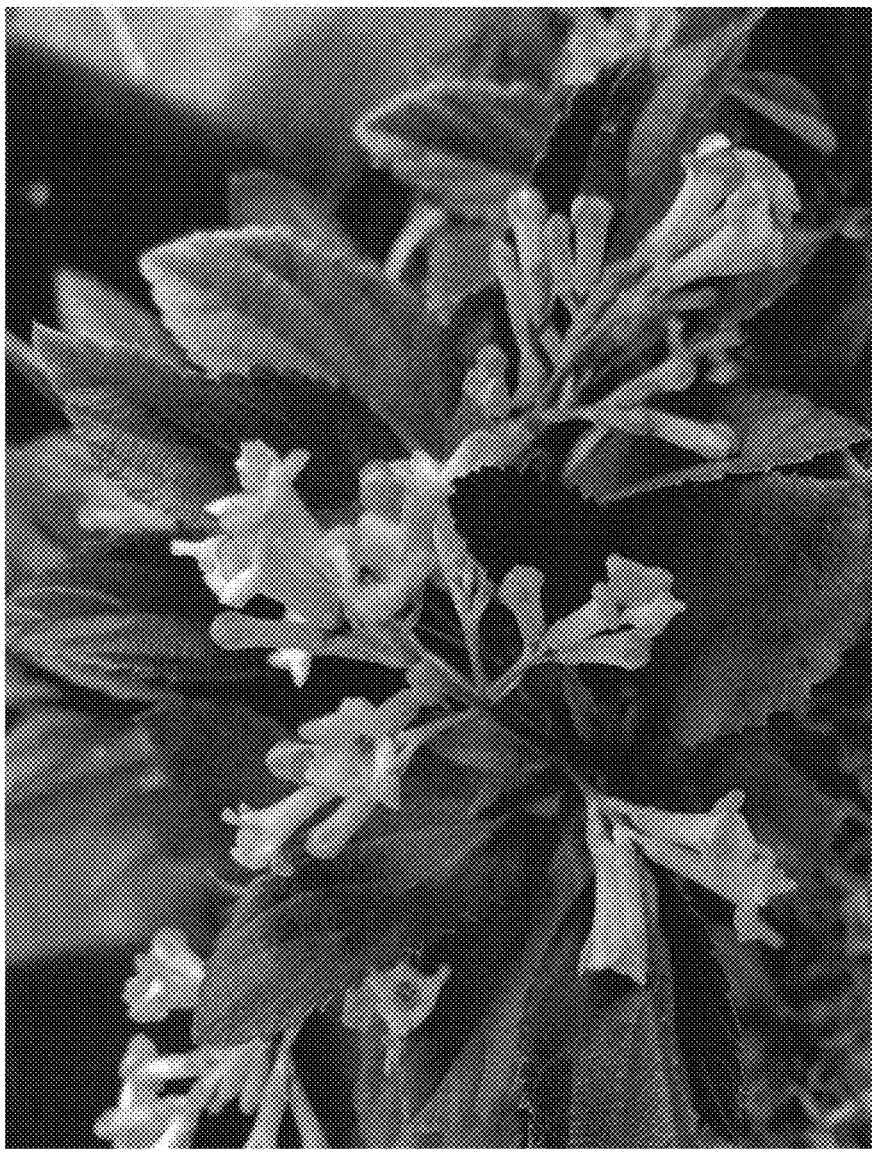
FIG. 1 is a color photograph showing pink inflorescences in March, 2020 in Mills River, N.C.
Figure 2:
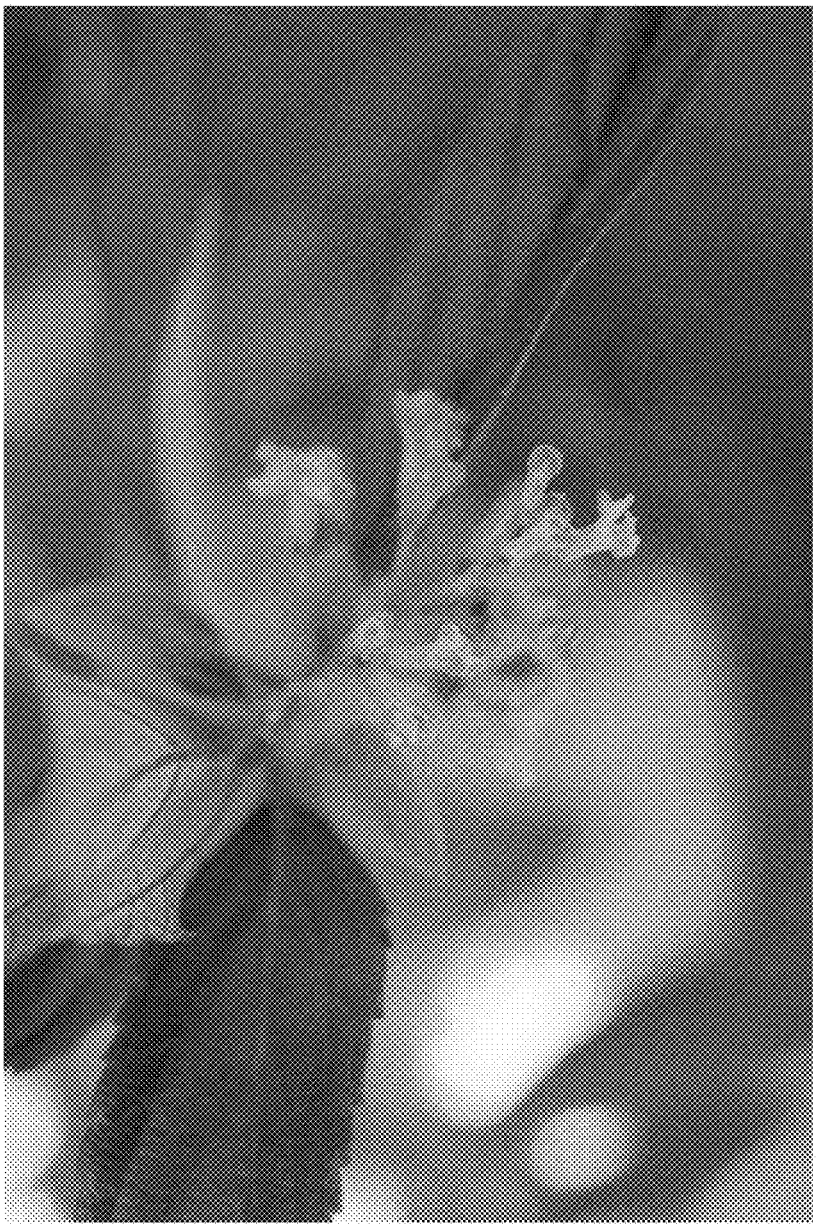
FIG. 2 is a color photograph showing the emerging foliage color of 'NCVX4' taken in March, 2020 in Mills River, N.C.
Figure 3:
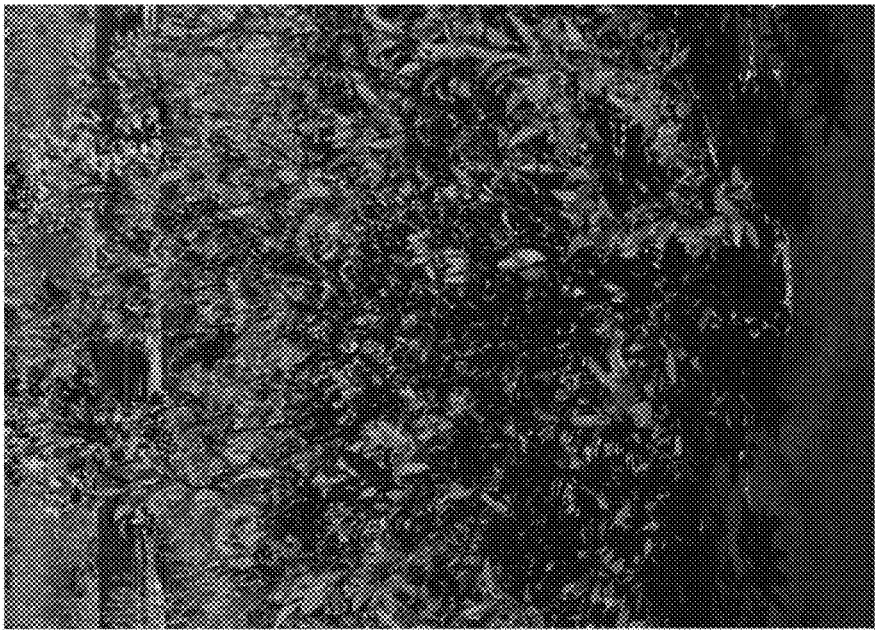
FIG. 3 is a color photograph of a field-grown 'NCVX4' taken in April, 2020 in Mills River, N.C.

The following is a detailed description of the botanical characteristics of the new and distinct *Viburnum* variety plant known by the denomination 'NCVX4'. The detailed description was taken on a five-year-old field-grown plant in Mills River, N.C. in 2019. All colors cited herein refer to The Royal Horticultural Society Colour Chart (The Royal Horticultural Society (R.H.S.), London, Sixth Edition). Where specific dimensions, sizes, colors, and other characteristics are given, it is to be understood that such characteristics are approximations or averages set forth as accurately as practicable.

Botanical classification: *Viburnum* hybrid 'NCVX4'.

PROPAGATION

Typical method: Softwood cuttings.

Time to initiate rooting: 28 days at approximately 27° C.

Time to produce a rooted young plant: About 3 months at approximately 27° C.

Root description: Dense, free branching roots of moderate thickness. Colored yellow-white, not accurately measured with an R.H.S. chart.

PLANT

Plant type: Perennial semi-evergreen flowering shrub.

Plant description:

- *Growth habit*.—Densely branched, compact, globose. Outer branches prostrate, inner branches upright. Plants moderately vigorous.
- *Height*.—50 to 70 cm.
- *Width*.—90 to 120 cm.

Shoot and stem:

- *Lateral branch length*.—Avg. 120 cm (100 to 150 cm).
- *Lateral branch diameter*.—Avg. 2 cm (1 to 5 cm).
- *Internode length*.—Avg. 4 cm (2 to 7 cm).
- *Immature shoot texture* (*current year*).—Glabrous.
- *Immature shoot color* (*current year*).—Brown (200B).
- *Mature stem texture* (*from prior year*).—Glabrous, with lenticels.
- *Mature stem color* (*from prior year*).—Grey (201A).

FOLIAGE

Leaf:

Type: Simple.

- *Persistence*.—Deciduous to semi-evergreen in warmer climates.
- *Arrangement*.—Opposite.
- *Shape*.—Ovate-lanceolate.
- *Apex*.—Acute.
- *Base*.—Cuneate.
- *Venation*.—Pinnate.
- *Vein color*.—Upper: Green (137A). Lower: Red-Purple (58A).
- *Margins*.—Serrate.
- *Emerging leaves*.—Color: Upper: Red-Purple (59B). Lower: Greyed-Purple (186D). Texture: Glabrous.
- *Mature leaves during growing season*.—Color: Upper: Green (137A). Lower: Yellow-Green (146B). Texture: Glabrous. Length of lamina: 2.2 cm to 6.0 cm. Width: 1.5 cm to 3.2 cm.
- *Fall/winter season*.—Color: Including Greyed-Purple (184C), Greyed-Orange (169C), and Green (139A) on both upper and lower surfaces.
- *Leaf attachment*.—Petiolate.
- *Petiole*.—Length: Avg. 0.8 cm (0.6 to 1 cm). Diameter: About 0.1 cm. Color: Red-Purple (58A). Texture: Glabrous.

FLOWER

Description: Single salverform flowers arranged on terminal cymes.

Number of true flowers per inflorescence: About 24.

Flowering season: February to early March in Mills River, N.C.

Fragrance: Fragrant.

Flower longevity: About 1 week.

Inflorescence:

- *Diameter*.—5 cm to 10 cm.
- *Height*.—3.0 cm to 4.5 cm.

Flower:

- *Diameter*.—Avg. 0.6 cm (0.4 to 0.7 cm).
- *Height*.—Avg. 1.4 cm (1.0 to 1.5 cm).

Bud:

- *Shape*.—Oblong.
- *Length*.—Avg. 0.8 cm (0.6 to 1.0 cm).
- *Diameter*.—About 0.2 cm.
- *Color*.—Red-Purple (62B) with Red-Purple (61C) at the tip.

Petals:

- *Number*.—5 fused petals.
- *Arrangement*.—Whorled.
- *Length*.—About 0.3 cm.
- *Width*.—About 0.2 cm.
- *Shape*.—Ovate.
- *Margin*.—Entire.
- *Apex*.—Obtuse.
- *Texture*.—Glabrous.
- *Color*.—Red-Purple (62B).

Sepal:

- *Number*.—5 fused sepals.
- *Arrangement*.—Whorled.
- *Length*.—About 0.4 cm.
- *Width*.—About 0.3 cm.
- *Shape*.—Ovate.
- *Margin*.—Entire.
- *Apex*.—Acute.
- *Base*.—Fused.
- *Texture*.—Slightly pubescent.
- *Color*.—Green (142B) with Red-Purple (60B) at the tip.

Peduncle:
*Length*.—About 2.5 cm.
*Diameter*.—About 1.5 cm.
*Texture*.—Pubescent.
*Color*.—Close to Yellow-Green (152C).
Pedicels:
*Length*.—About 0.3 cm.
*Diameter*.—Less than 0.1 cm.
*Texture*.—Pubescent.
*Color*.—Close to Yellow-Green (147C).

REPRODUCTIVE ORGANS

Gynoecium:
*Pistil number*.—1.
*Pistil length*.—Less than 0.1 cm.
*Stigma shape*.—Rounded.
*Stigma color*.—Red-Purple (60A).
*Style length*.—Less than 0.1 cm.
*Style color*.—Red-Purple (60A).

Androecium:
*Stamen number*.—5.
*Anther shape*.—Oblong.
*Anther size*.—About 0.1 cm.
*Anther color*.—Black (202A).
*Amount of pollen*.—Average.
*Pollen color*.—Yellow (8A).

OTHER CHARACTERISTICS

Fruit and seed: None observed.
Disease and insect resistance: No significant resistance nor susceptibility to disease or insect pests has been observed.
Cold hardiness: At least USDA zone 6b; testing has not been completed in colder zones.

What is claimed is:

1. A new and distinct cultivar of *Viburnum* plant named 'NCVX4' as herein illustrated and described.

* * * * *